July 11, 1972 W. H. JESSEL, JR., ET AL Plant Pat. 3,232
CHRYSANTHEMUM PLANT
Filed Nov. 12, 1970
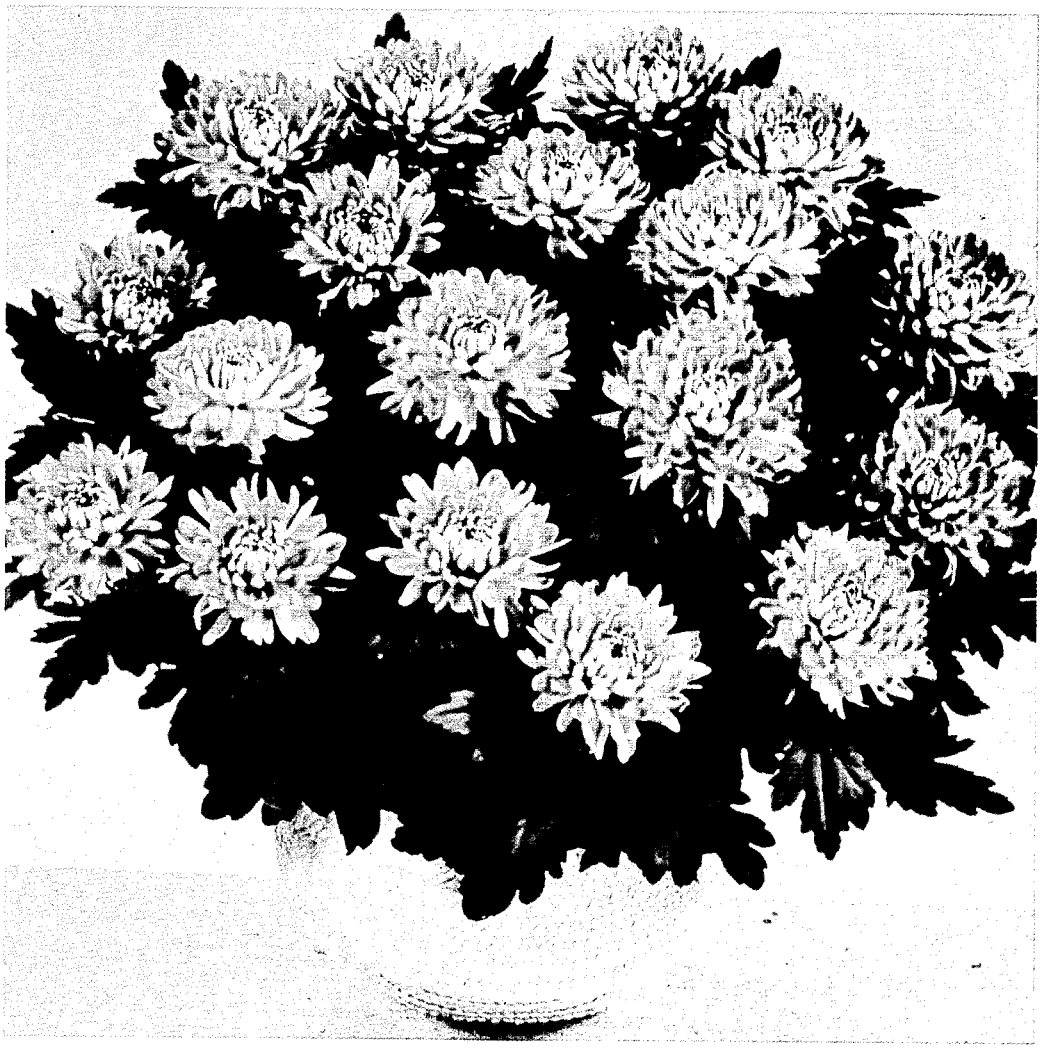
INVENTORS
WALTER H. JESSEL, Jr.
WILLIAM E. DUFFETT
BY Oberlin, Maky, Donnelly & Renner
ATTORNEYS

United States Patent Office

Plant Pat. 3,232
Patented July 11, 1972

3,232

CHRYSANTHEMUM PLANT

Walter H. Jessel, Jr., Doylestown, and William E. Duffett, Akron, Ohio, assignors to Yoder Brothers, Inc., Barberton, Ohio

Filed Nov. 12, 1970, Ser. No. 89,152
Int. Cl. A01h *5/00*
U.S. Cl. Plt.—82 1 Claim

The present invention comprises a new and distinct cultivar of chrysanthemum plant which is a sport of the well-known, unpatented cultivar known in the United States as Mandalay.

The new cultivar is similar in many respects to Mandalay, having the same characteristics of:

(1) Foliage size.
(2) Foliage shape.
(3) Foliage color.
(4) Response.
(5) Flower size.
(6) Flower form.

The new cultivar is distinguished from Mandalay by the following characteristics:

(1) A darker red bronze color, compared to the orange bronze color of the parent cultivar.

The new cultivar was selected from a flowering block of the parent cultivar at Yoder Brothers, Inc., in Barberton, Ohio, and when asexually reproduced by cuttings has been found to retain its distinctive characteristics through successive propagations.

The new cultivar when grown in the vicinity of Barberton, Ohio, has a response period of approximately 10 weeks. The response time, blooming period, color, and total vigor may vary significantly with varying environmental conditions such as temperature, day length, and light intensity. Suggested flowering in the northern and western United States is from March through November. In the south, from November through June. In Florida, from December through April, and in coastal California, year round.

The accompanying drawing shows the unique color characteristic of the new cultivar, the color being as nearly true as possible with color illustrations of this type.

The following data is based on observations made of the new variety in a greenhouse at Barberton, Ohio. Color references are to the Munsell Color Book, 1963 edition, and comparisons in color made with the cultivar Mandalay.

Botanical classification: *Chrysanthemum morifolium.*

Bloom:
*Size.*—3½"–4".
*Fully expanded.*—5".
*Borne.*—Terminal on disbudded branches.
*Stems.*—Branches 10"–16".
*Form.*—Semi-incurved.
*Permanence.*—14–18 days.

| | Glowing Mandalay | Mandalay |
|---|---|---|
| Color: | | |
| Center of flower | Greenish yellow, 7.5Y8/10 | Greenish yellow, 7.5Y7/10. |
| Base of petals | Red bronze, 5Y3/8 over yellow, 5Y8.5/10, to yellow bronze, 10YR6/10 over yellow, 5Y8.5/10. | Yellow bronze, 10YR7/12 to yellow, 5Y8.5/10. |
| Inside of petals | Red bronze, 5R3/8 over yellow, 5Y8.5/10, to yellow bronze, 10YR6/10 over yellow, 5Y8.5/10. | Do. |
| Tonality from a distance. | Dark bronze | Light bronze. |
| Discoloration | Light bronze | Light yellow bronze. |

Petals:
*Texture.*—Smooth.
*Appearance and form.*—Broadly keeled, tapering to a point.
*Arrangement.*—Composite, whorled on a single receptacle.
*Persistence.*—Resists shatter.
*Fragrance.*—Typical chrysanthemum.

Reproductive organs:
*Stamen, anthers.*—None to 30.
*Pollen.*—None to scant.
*Arrangement.*—Clustered in center of flower, if present.
*Styles.*—Present both ray and disc florets.
*Length.*—Short.
*Ovaries.*—At the base of petal attached to receptacle.

Plant:
*Form.*—Herbaceous.
*Growth.*—Semi-upright.
*Height,* depending on culture.—10"–16".
*Spread,* depending on culture.—6"–10".

Foliage:
*Top side.*—Dark green, 10GY2/4.
*Size.*—5¾" long, 3¾" wide.
*Quantity.*—Numerous.
*Shape.*—Spatulate lobed.
*Texture.*—Smooth.
*Ribs and veins.*—Prominent.
*Edge.*—Moderately indented.
*Serration.*—Slight.
*Underside.*—Light green, 7.5GY5/4.
*Stipules.*—Rudimentary to prominent.

We claim:

1. A new and distinct cultivar of chrysanthemum characterized particularly as to uniqueness as compared to the parent cultivar Mandalay by its darker red bronze color.

No references cited.

ROBERT E. BAGWILL, Primary Examiner